United States Patent [19]

Kelly

[11] Patent Number: 5,532,358
[45] Date of Patent: Jul. 2, 1996

[54] METHOD FOR PREPARING ALKYL-5,11-DIHYDRO-6H-DIPYRIDO-[3,2-B:2',3'-E] [1,4] DIAZEPIN-6-ONES

[75] Inventor: Terence A. Kelly, Ridgefield, Conn.

[73] Assignee: Boehringer Ingelheim Pharmaceuticals, Inc., Ridgefield, Conn.

[21] Appl. No.: 321,710

[22] Filed: Oct. 12, 1994

[51] Int. Cl.⁶ .................... C07D 471/14; A61K 31/55
[52] U.S. Cl. .................................................. 540/495
[58] Field of Search .................... 540/495; 514/220

[56] References Cited

U.S. PATENT DOCUMENTS

| | | | |
|---|---|---|---|
| 5,087,625 | 2/1992 | Hargrave et al. | 540/495 |
| 5,366,972 | 11/1994 | Hargrave et al. | 540/495 |

*Primary Examiner*—Robert T. Bond
*Attorney, Agent, or Firm*—Robert P. Raymond; Alan R. Stempel; Mary-Ellen M. Timbers

[57] ABSTRACT

A method for preparing certain 4-alkyl-5,11-dihydro-6H-dipyrido[3,2-b:2',3'-e][1,4]diazepin-6-ones, which employs the following reaction scheme:

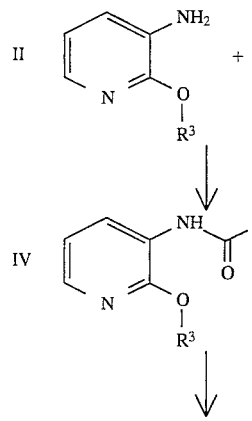

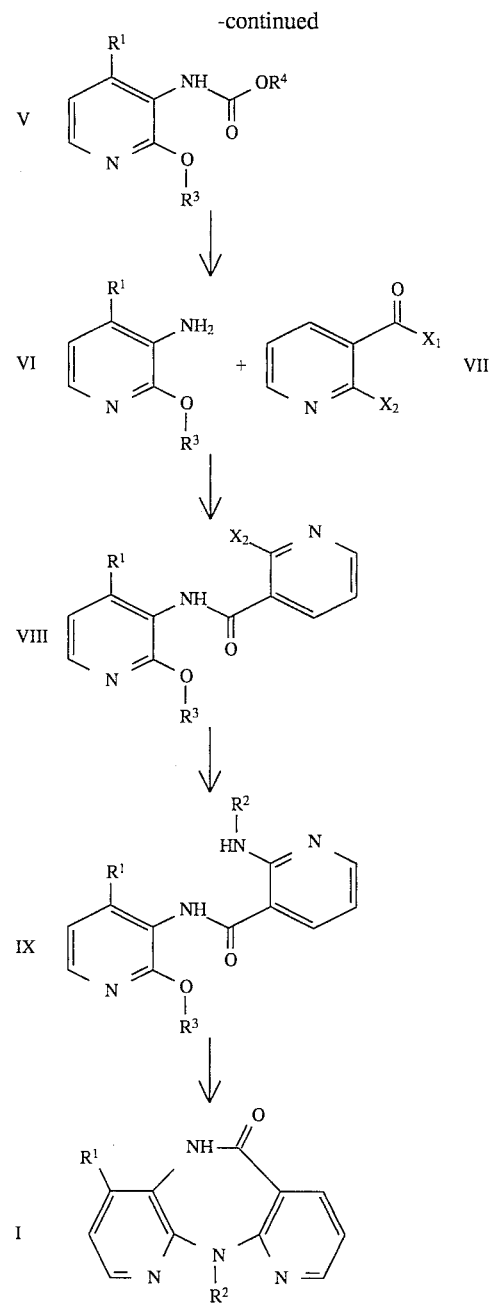

6 Claims, No Drawings

METHOD FOR PREPARING ALKYL-5,11-DIHYDRO-6H-DIPYRIDO[3,2-B:2',3'-E][1,4] DIAZEPIN-6-ONES

FIELD OF THE INVENTION

This invention relates to a novel method for preparing certain 4-alkyl-5,11-dihydro-6H-dipyrido[3,2-b:2',3'-e][1,4]diazepin-6-ones.

BACKGROUND OF THE INVENTION

4-Alkyl-5,11-dihydro-6H-dipyrido[3,2-b:2',3'-e][1,4]diazepin-6-one, and their use in the treatment of HIV-1 infection are known in the prior art. These compounds are, for example, described in copending U.S. patent application Ser. No. 08/091,418 filed Jul. 13, 1993, European Patent Application No. 90 121 954.3 (publication No. 0 429 987), and by Karl D. Hargrave et al., "Novel Non-Nucleoside Inhibitors of HIV-1 Reverse Transcriptase. 1. Tricyclic Pyridobenzo- and Dipyridodiazepinones", J. Med. Chem, 34, 2231 (1991). Copending U.S. patent application Ser. No. 08/063,592, filed on May 18, 1993 describes one of several possible methods for preparing 5,11-dihydro-6H-dipyrido[3,2-b:2',3'-e][1,4]diazepines, and U.S. Pat. No. 5,200,522 describes methods for preparing 4-alkyl-3-amino-2-chloropyridines useful as intermediates in the synthesis of 5,11-dihydro-6H-dipyrido[3,2-b:2',3'-e][1,4]diazepines.

SUMMARY OF THE INVENTION

4-Alkyl-5,11-dihydro-6H-dipyrido[3,2-b:2',3'-e][1,4]diazepin-6-ones prepared by the novel process of this invention have the formula:

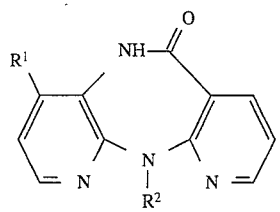

wherein, $R^1$ is alkyl of 1 to 6 carbon atoms, trihalomethyl, alkyloxyalkyl or alkylthioalkyl of 2 to 5 carbon atoms, or arylalkyl (wherein the aryl moiety is phenyl, thienyl, furanyl, or pyridyl, which is either unsubstituted or substituted by alkyl or alkoxy of 1 to 3 carbon atoms, or halogen, and the alkyl moiety contains 1 to 2 carbon atoms which may be unsubstituted or substituted with a methyl group); and, $R^2$ is alkyl of 1 to 6 carbon atoms or cycloalkyl of 3 to 6 carbon atoms.

The process of the invention for the preparation of the compound of formula I is depicted by the following reaction scheme.

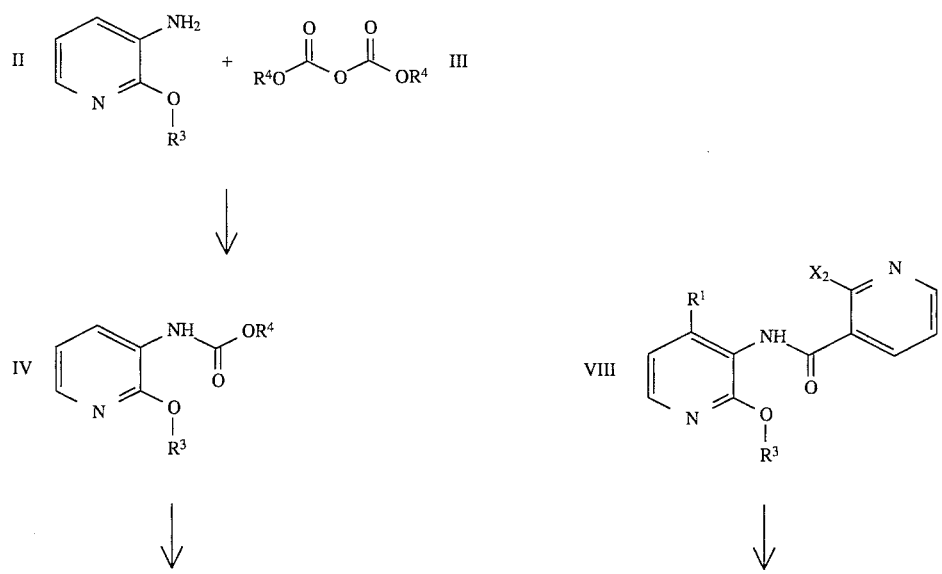

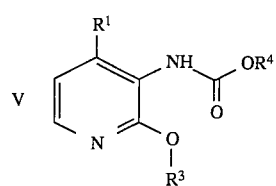

V

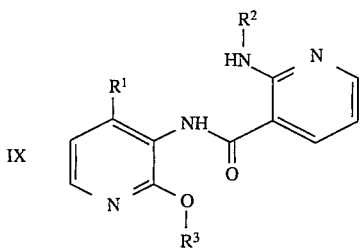

IX

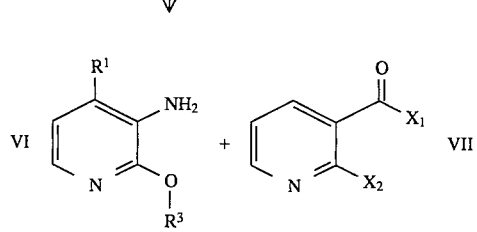

VI + VII

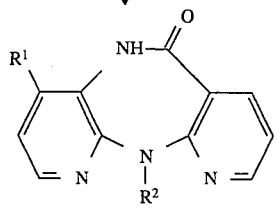

I

DETAILED DESCRIPTION OF THE INVENTION

The process of this invention for preparing the 4-alkyl-5,11-dihydro-6H-dipyrido[3,2-b:2',3'-e][1,4]diazepin-6-ones of formula I comprises the following steps:

Step 1: A compound of the formula II

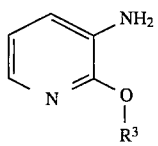
(II)

wherein $R^3$ is alkyl of from 1 to 3 carbon atoms, is reacted with a compound of the formula III

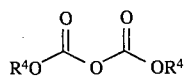
(III)

wherein $R^4$ is an alkyl group of from one to 5 carbon atoms, in an aprotic, organic solvent such as, but not limited to, tetrahydrofuran (THF), with two equivalents of a base such as, but not limited to, sodium hexamethyldisilazane (NaHMDS), at room temperature for about 15 minutes to two hours, to produce a compound of the formula IV

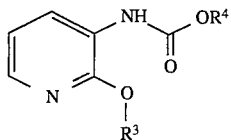
(IV)

Step 2: The compound of formula IV, produced in Step 1, is reacted with two equivalents of a strong base, such as, for example, n-butyllithium (nBuLi), at between about −78° and −10° C. in a polar, aprotic solvent, such as, for example, diethyl ether, containing a strongly polar, aprotic cosolvent, such as, for example, tetramethylethylenediamine (TMEDA), to generate an intermediate dianionic species. The dianionic species need not be isolated from the reaction mixture. The reaction mixture, containing the dianionic species is then cooled to below about −30° C. and treated with an electrophile of the form $R^1$—X, wherein $R^1$ is as described above, and X is a leaving group, such as, for example, halogen, to generate a compound of formula V upon stirring at between about 0° and 30° C. for about 1 to 12 hours.

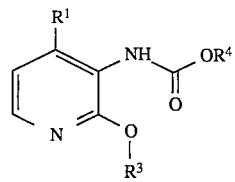
(V)

Step 3: The protecting group (—COOR⁴) is removed from the compound of formula V, produced in Step 2, using known per se techniques, such as those described by Greene in "Protective Groups in Organic Synthesis" (J. Wiley & Sons, 1981) to yield a compound of the formula VI.

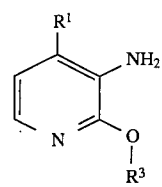
(VI)

For example, when $R^4$ is tert-butyl, the reaction proceeds using dry hydrogen chloride in ethyl acetate at about room temperature. The free base of the amine may be liberated using a base, such as, for example, NaHCO₃. When $R^4$ is methyl, base catalyzed hydrolysis may be used.

Step 4: The compound of formula VI, produced in step 3, is reacted with a compound of the formula VII

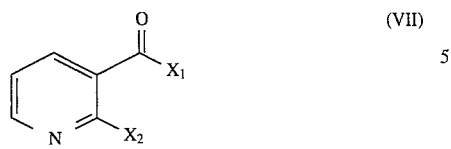

wherein $X_1$ and $X_2$ are halogen atoms, such as, for example, chlorine, in an aprotic organic solvent such as, for example, ethyl acetate, in the presence of a hydrogen halide (HX) scavenger such as, for example, triethylamine, to produce a compound of the formula VIII.

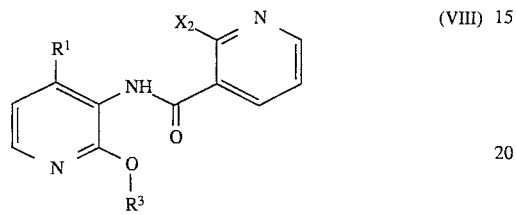

Step 5: The compound of formula VIII, produced in step 4, is reacted with an amine of the formula $R^2$—$NH_2$ wherein $R^2$ is as described above, at a temperature of between about 90° and 120° C. for about 3 to 24 hours, in the presence of a hydrogen halide scavenger (HX), such as, for example, $R^2$—$NH_2$, to produce a compound of the formulaIX.

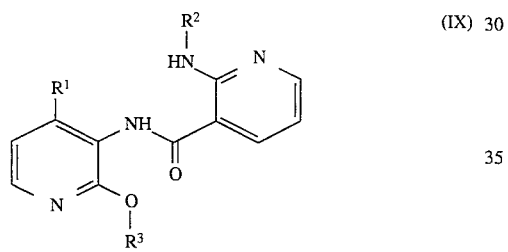

Step 6: The compound of formula IX, produced in step 5, is reacted with 2 equivalents of a base such as, for example, NaH, in a highly polar, aprotic organic solvent, such as, for example, pyridine, at between about 80° and 110° C. for about 2 to 24 hours, to produce a compound of formula I.

Example I illustrates the preparation of a 4-alkyl-5,11-dihydro-6H-dipyrido[3,2-b:2',3'-e][1,4]diazepin-6-one, a compound of formula I wherein $R^1$ is methyl, using the synthetic method provided by the present invention.

EXAMPLE I

A) Preparation of
3-(tert-Butoxycarbonylamino)-2-methoxypyridine

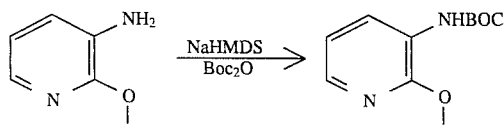

To a stirred solution of 2.48 g (20 mmol) of 3-amino-2-methoxypyridine and 4.37 g (20 mmol) of di-tert-butyldicarbonate (Boc₂O) in 10 mL of THF was added at 0° C. 40 mL of a 1 M solution of NaHMDS in THF. The mixture was then stirred at room temperature for 2 hours. The THF was removed by rotary evaporation and the residue was dissolved in EtOAc and washed twice with an equal volume of 0.1N HCl. The EtOAc layer was dried (MgSO₄) and concentrated to give 3.9 g (87%) of the desired material as an oil after purification further by flash chromatography on silica gel using 95:5 hexane:EtOAc as the eluant.

B) Preparation of 3-(tert-Butoxycarbonylamino)-2-methoxy-4-methylpyridine

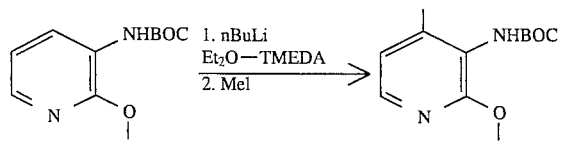

To a stirred solution of 1.12 g (5 mmol) of 3-(tert-butoxycarbonylamino)-2-methoxypyridine in 25 mL of dry ether containing 1.8 mL, (12 mmol) of TMEDA at −78° C. under an argon atmosphere was added 4.8 mL (12 mmol) of a 2.5M solution of nBuLi in hexanes. The mixture was then warmed to −10° C. for 2 h. Recooling to −78° C. and treatment with iodomethane (0.99 g, 7 mmol) followed by warming to room temperature for 1 h produced the desired product which was purified by quenching with water, washing the ether layer with 0.1N HCl, drying (MgSO₄), concentration and flash chromatography (9:1 hexanes:EtOAc). Yield: 1.00 g (84%). Recrystallization from heptane provided further purification. m.p.: 93°–95° C.

C) Preparation of
3-Amino-2-methoxy-4-methylpyridine

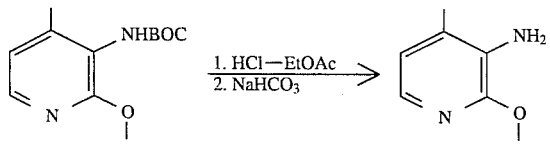

3-(tert-Butoxycarbonylamino)-2-methoxy-4-methylpyridine (0.7 g, 2.9 mmol) was treated with 25 mL of 4M HCl in EtOAc at room temperature overnight. The resulting suspension was carefully washed with sat. NaHCO₃, dried (MgSO₄) and concentrated to give 0.4 g of the free amine as an oil (100%). m.p. (HCl salt): 199° C. (d).

D) Preparation of 2-Chloro-N-(2-methoxy-4-methyl-3-pyridinyl)-3-pyridinecarboxamide

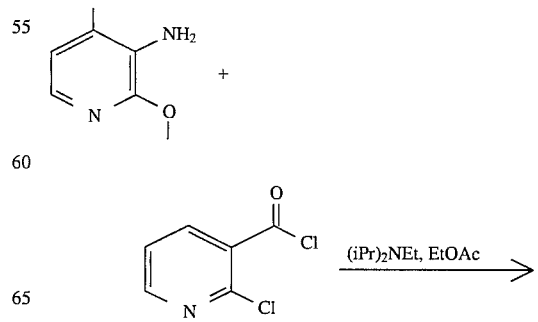

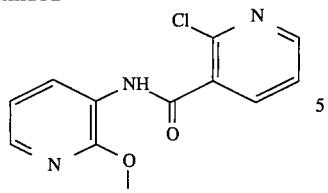

To a solution of 0.4 g (2.9 mmol) of 3-amino-2-methoxy-4-methylpyridine and 0.5 g (2.9 mmol) of 2-chloronicotinoyl chloride in EtOAc at 0° C. was added 0.4 g (3.0 mmol) of N,N-diisopropylethylamine. Stirring was continued for 10 h at which point the mixture was washed with 0.1N HCl, dried (MgSO$_4$), concentrated and purified by flash chromatography on silica gel (1:1 EtOAc:hexanes) to yield 0.7 g (88%) of the desired material. m.p.: 145°–146° C. (Recrystallized from ethyl acetate).

E) Preparation of 2-(Cyclopropylamino)-N-(2-methoxy-4-methyl-3-pyridinyl)-3-pyridinecarboxamide

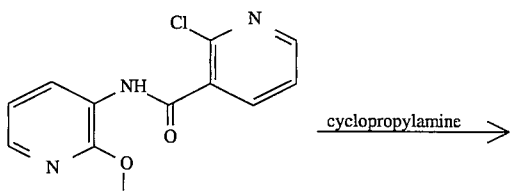

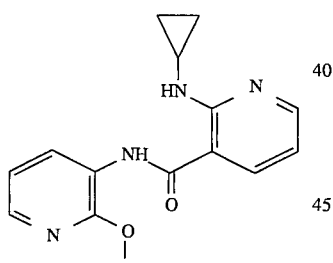

2-Chloro-N-(2-methoxy-4-methyl-3-pyridinyl)-3-pyridinecarboxamide (0.55 g, 2 mmol) was placed in a sealed tube containing cyclopropylamine (0.5 mL, 7 mmol) and heated to 110° C. overnight. Removal of the cyclopropylamine by rotary evaporation followed by flash chromatography of the residue on silica gel (1:1 EtOAc:hexanes) gave the desired compound in 86% yield (0.51 g). m.p.: 151°–152° C. (Recrystallized from heptane).

F) Preparation of 5,11-dihydro-4-Methyl-6H-dipyrido-[3,2-b:2',3'-e][1,4]diazepin-6-one

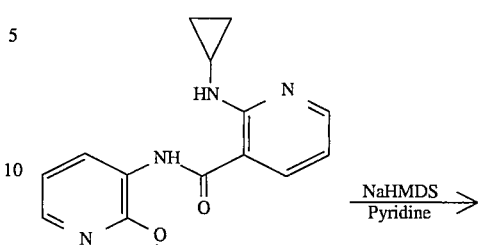

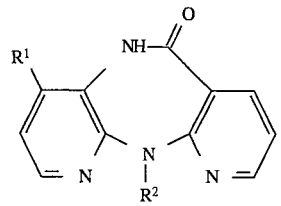

A solution of 2-(cyclopropylamino)-N-(2-methoxy-4-methyl-3-pyridinyl)-3-pyridinecarboxamide (0.3 g, 1 mmol) in 2 mL of dry pyridine under an argon atmosphere was treated with 2.2 mL of a 1.0M solution of NaHMDS. The solution was then warmed to 90° C. for 6 h. Upon cooling, the mixture was partitioned between EtOAc and 0.5N HCl. The EtOAc layer was then washed further with 0.5N HCl, dried (MgSO$_4$) and concentrated. The residue was purified by flash chromatography on silica gel (1:1 EtOAc:Hexanes) to give 5,11-dihydro-4-methyl-6H-dipyrido[3,2-b:2',3'-e][1,4] diazepin-6-one in 91% yield (0.24 g).

What is claimed is:

1. A method for preparing 4-alkyl-5,11-dihydro-6H-dipyrido[3,2-b:2',3'-e][1,4]diazepin-6-ones of the formula I

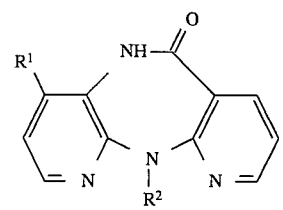

wherein

R$^1$ is alkyl of 1 to 6 carbon atoms, trihalomethyl, alkyloxyalkyl or alkylthioalkyl of 2 to 5 carbon atoms, alkylthio of 1 to 5 carbon atoms, or arylalkyl (wherein the aryl moiety is phenyl, thienyl, furanyl, or pyridyl, which is either unsubstituted or substituted by alkyl or alkoxy of 1 to 3 carbon atoms, or halogen, and the alkyl moiety contains 1 to 2 carbon atoms which may be unsubstituted or substituted with a methyl group);

and,

R$^2$ is alkyl of 1 to 6 carbon atoms or cycloalkyl of 3 to 6 carbon atoms, which comprises the steps of:

a) reacting a compound having the formula II

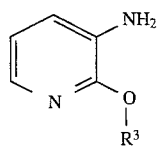

wherein $R^3$ is alkyl of from one to 3 carbon atoms, with a compound of the formula III

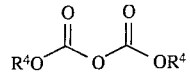

wherein $R^4$ is an alkyl group of from one to 5 carbon atoms, in an aprotic, organic solvent, and in the presence of two equivalents of a base, to produce a compound of the formula IV

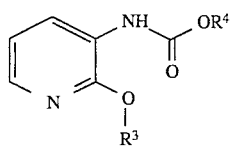

wherein $R^3$ and $R^4$ are as hereinbefore defined;

b) reacting the compound of formula IV with two equivalents of a strong base, in a polar, aprotic, organic solvent containing a strongly polar, aprotic cosolvent, to generate an intermediate dianionic species, and further reacting the intermediate dianionic species, which is not isolated from the reaction mixture, with an electrophile of the formula $R^1$—X, wherein $R^1$ is described above, and X is a leaving group, to generate a compound of the formula V;

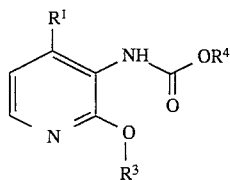

c) removing the protecting group (—$COOR^4$) from the compound of the formula V by cleavage of the carbamate, to yield a compound of the formula VI

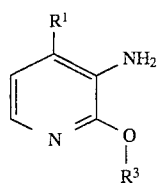

d) reacting the compound of formula VI with a compound of the formula VII

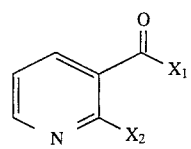

wherein $X_1$ and $X_2$ may be the same or different and are each a halogen atom, in an aprotic, organic solvent in the presence of a hydrogen halide scavenger, to produce a compound of the formula VIII

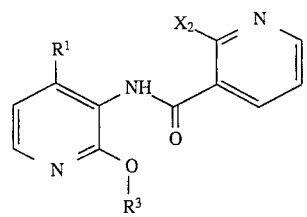

wherein $R^1$, $R^3$ and $X_2$ are as hereinbeforedefined;

e) reacting the compound of formula VIII with an amine of the formula $R^2$—$NH_2$, wherein $R^2$ is as hereinbefore defined, in the presence of a hydrogen chloride scavenger, to produce a compound of the formula IX

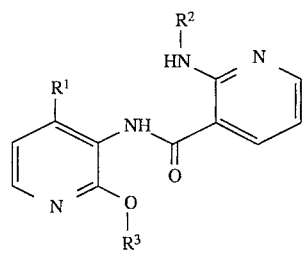

and, f) reacting the compound of formula IX with 2 equivalents of a base, in a polar, aprotic, organic solvent, to produce the compound of formula I.

2. The process as recited in claim 1, wherein $R^3$ is methyl and $R^4$ is tert-butyl.

3. The process as recited in claim 1 wherein:

i) the organic solvent employed in step (a) is THF and the base employed in step (a) is NaH, $NaNH_2$ or NaHMDS;

ii) the strong base employed in step (b) is n-butyllithium and the solvent and cosolvent employed in step (b) are, respectively, diethylether and TMEDA;

iii) the protecting group employed in step (c) is removed using dry hydrogen chloride in ethyl acetate and the resulting hydrochloride salt is converted to its free amine by treatment with $NaHCO_3$;

iv) the organic solvent employed in step (d) is ethyl acetate and the hydrogen chloride scavenger employed in step (d) is a trialkyl amine;

v) the hydrogen chloride scavenger employed in step (e) is CaO or $R_2$—$NH_2$; and vi) the base employed in step (f) is NaH, $NaNH_2$ or NaHMDS.

4. A method for preparing nevirapine, which is also known by the chemical name 11-cyclopropyl-5,11-dihydro-4-methyl-6H-dipyrido[3,2-b:2',3'-e][1,4]diazepin-6-one and by the following chemical structure

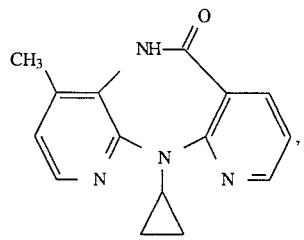

which method comprises the steps of:

a) reacting a compound having the formula II

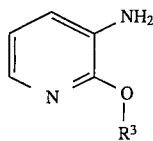 (II)

wherein R³ is alkyl of from one to 3 carbon atoms, with a compound of the formula III

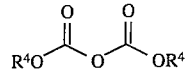 (III)

wherein R⁴ is an alkyl group of from one to 5 carbon atoms, in an aprotic, organic solvent, and in the presence of two equivalents of a base, to produce a compound of the formula IV

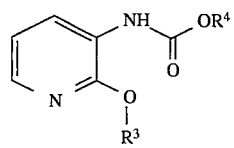 (IV)

wherein R³ and R⁴ are as hereinbefore defined;

b) reacting the compound of formula IV with two equivalents of a strong base, in a polar, aprotic, organic solvent containing a strongly polar, aprotic cosolvent, to generate an intermediate dianionic species, and further reacting the intermediate dianionic species, which is not isolated from the reaction mixture, with an electrophile of the formula CH₃—X, wherein X is a leaving group, to generate a compound of the formula;

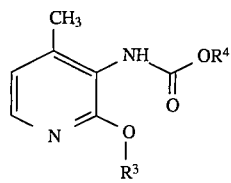

c) removing the protecting group (—COOR⁴) from the compound produced in the prior step by cleavage of the carbamate, to yield a compound of the formula

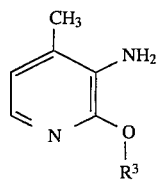

d) reacting the compound produced in the prior step with a compound of the formula VII

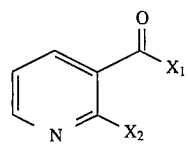 (VII)

wherein X1 and X2 may be the same or different and are each a halogen atom, in an aprotic, organic solvent in the presence of a hydrogen halide scavenger, to produce a compound of the formula

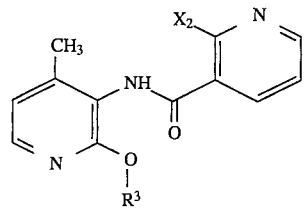

wherein R³ and X₂ are as hereinbefore defined;

e) reacting the compound produced in the prior step with an amine of the formula

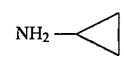

in the presence of a hydrogen chloride scavenger, to produce a compound of the formula

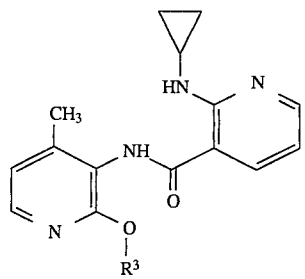

and, f) reacting the compound produced in the prior step with 2 equivalents of a base, in a polar, aprotic, organic solvent, to produce nevirapine.

5. The process as recited in claim 4, wherein R³ is methyl and R⁴ is tert-butyl.

6. The process as recited in claims 4 or 5 wherein:

i) the organic solvent employed in step (a) is THF and the base employed in step (a) is NaH, NaNH₂ or NaHMDS;

ii) the strong base employed in step (b) is n-butyllithium and the solvent and cosolvent employed in step (b) are, respectively, diethylether and TMEDA;

iii) the protecting group employed in step (c) is removed using dry hydrogen chloride in ethyl acetate and the resulting hydrochloride salt is converted to its free amine by treatment with NaHCO₃;

iv) the organic solvent employed in step (d) is ethyl acetate and the hydrogen chloride scavenger employed in step (d) is a trialkyl amine;

v) the hydrogen chloride scavenger employed in step (e) is CaO or

; and, vi) the base employed in step (f) is NaH, NaNH₂ or NaHMDS.

* * * * *